US008889680B2

(12) United States Patent (10) Patent No.: US 8,889,680 B2
Krysan et al. (45) Date of Patent: Nov. 18, 2014

(54) TREATMENT OR PREVENTION OF FUNGAL INFECTIONS WITH PDK1 INHIBITORS

(75) Inventors: Damian Krysan, Pittsford, NY (US);
Louis DiDone, Rochester, NY (US);
Bonnie K. Baxter, Fairport, NY (US)

(73) Assignee: University of Rochester, Rochester, NY (US)

( * ) Notice: Subject to any disclaimer, the term of this patent is extended or adjusted under 35 U.S.C. 154(b) by 108 days.

(21) Appl. No.: 13/298,766

(22) Filed: Nov. 17, 2011

(65) Prior Publication Data

US 2012/0122872 A1 May 17, 2012

Related U.S. Application Data

(60) Provisional application No. 61/414,660, filed on Nov. 17, 2010.

(51) Int. Cl.
*A01N 43/64* (2006.01)
*A01N 37/18* (2006.01)
*A61K 38/00* (2006.01)
*A61P 31/10* (2006.01)

(52) U.S. Cl.
USPC .......................................... 514/243; 514/3.3

(58) Field of Classification Search
USPC ....................................................... 514/243
See application file for complete search history.

(56) References Cited

FOREIGN PATENT DOCUMENTS

WO    WO0036135 A2 *  6/2000

OTHER PUBLICATIONS

Li et al. (Experimental and Molecular Therapeutics 6: Targeting Signaling Pathways 1 Abstract #665 Novel small molecule inhibitors for pancreatic cancer. Proc Amer Assoc Cancer Res, vol. 46, 2005).*
Troke et al. (Efficacy of UK-49,858 (fluconazole) against *Candida albicans* experimental infections in mice. Antimicrobial agents and chemotherapy 28.6 (1985): 815-818).*
Pandeya et al., "Synthesis, antibacterial, antifungal, and anti-HIV evaluation of Schiff and Mannich bases of isatin derivatives with 3-amino-2-methylmercaptoquinazolin-4(3H)-one," Pharm. Acta. Helv. 74:11-17 (1999).
Pandey et al., "Benzimidazolyl quinolinyl mercaptotriazoles as potential antimicrobial and antiviral agents," Acta Pharm. 55(1):47-56 (2005).
Paravincini et al., "The *Candida albicans* PKC1 gene encodes a protein kinase C homolog necessary for cellular integrity but not dimorphism," Yeast 12:741-56 (1996).
Peifer and Alessi, "Small-molecule inhibitors of PDK1," Chem. MedChem. 3:1810-38 (2008).
Pfaller et al., "Epidemiology of invasive candidiasis: persistent public health problem," Clin. Microbiol. Rev. 20:133-63 (2007).
Pierce et al., "A simple and reproducible 96-well plate based method for the formation of fungal biofilms and its application to antifungal susceptibility testing," Nat. Protoc. 3:1494-1500 (2008).
Roelants et al., "Pkh1 and Pkh2 differentially phosphorylate and activate Ypk1 and Ykr2 and define proteinase modules required for cell wall integrity," Mol. Biol. Cell 13:3005-28 (2002).
Roelants et al., "Differential roles of PDK1- and PDK2-phosphorylation sites in the yeast AGC kinases Ypk1, Pkc1, and Sch9," Microbiol. 150:3289-304 (2004).
Roelants et al., "A protein kinase network regulates the function of aminophospholipid flippases," Proc. Natl. Acad. Sci. USA 107:34-9 (2010).
Sridhar et al., "Anticonvulsant activity of hydrazones, Schiff and Mannich bases of isatin derivatives," Eur. J. Pharm. Sci. 16:129-132 (2002).
Sussman et al., "Discovery of cercosporamide, a known antifungal natural product as a selective Pkc1 kinase inhibitor through high-throughput screening," Eukaryotic Cell 3:932-43 (2004).
Voodeckers et al., "Yeast phosphoinositide-dependent protein kinase-1 (PDK1) orthologs Pkh1-1 differentially regulate phosphorylation of protein kinase A (PKA) and the protein kinase B(PKB)/S6K ortholog Sch9," J. Biol. Chem 286:22017-27 (2011).
Walther et al. "Pkh-kinases control eisosome assembly and organization," EMBO J 26:4946-55 (2007).
Wang et al., "The *Candida albicans* Sur7 protein is needed for proper synthesis of the fibrillar component of the cell wall that confers strength," Eukaryot. Cell 10:72-80 (2011).
Walsh et al., "Repurposing libraries of eukaryotic protein kinase inhibitors for antibiotic discovery," Proc. Natl. Acad. Sci. USA 106:1689-90 (2009).
Weinblatt et al., "An oral spleen tyrosine kinase (Syk) inhibitor for rheumatoid arthritis," N. Engl. J. Med. 363:1303-12 (2010).
Zeng et al., "Simultaneous inhibition of PDK1/Akt and Fms-like tyrosine kinase 3 signaling by a small-molecule KP 372-1 induces mitochondrial dysfunction and apoptosis in acute myelogenous leukemia," Cancer Res. 66:373-46 (2006).
Zhu et al., "From the cyclooxygenase-2 inhibitor celecoxib to a novel class of 3-phosphoinositide-dependent kinase-1 inhibitors," Cancer Res. 64:4309-18 (2004).
AbdulHameed et al., "Microscopic modes and free energies of 3-phosphoinositide-dependent kinase-1 (PDK1) binding with celecoxib and other inhibitors," J. Phys. Chem B 110:26365-74 (2006).
Afeltra and Verweij, "Antifungal activity of nonantifungal drugs," Eur. J. Clin. Microbiol. Infect. Dis. 22:397-407 (2003).
Angiolini et al., "Structure-based optimization of potent PDK1-inhibitors," Bioorg. Med. Chem. Lett. 20:4095-9 (2010).
Baxter et al., "Phosphoinositide-dependent kinase 1 (PDK1) inhibitors are a novel class of wall-targeted antifungal small molecules," American Society for Microbiology ICAAC Poster Presentation, Boston, MA (Abstract) (Sep. 2010).

(Continued)

*Primary Examiner* — Layla Soroush
(74) *Attorney, Agent, or Firm* — Kilpatrick Townsend & Stockton, LLP

(57) ABSTRACT

Provided are methods of treating or preventing a fungal infection in a subject. The methods comprise identifying a subject with or at risk of developing a fungal infection and administering to the subject a therapeutically effective amount of an inhibitor or a fungal phosphoinositide-dependent kinase 1 (PDK-1) or a homolog thereof. Inhibition of the fungal PDK-1 or homolog thereof results in the treatment or prevention of a fungal infection in the subject. Also provided are compositions comprising an inhibitor of a fungal phosphoinositide-dependent kinase 1 (PDK-1) or a homolog thereof, and a pharmaceutically acceptable carrier.

3 Claims, 10 Drawing Sheets

(56) References Cited

OTHER PUBLICATIONS

Baxter et al., "Identification, in vitro activating and mode of action of phosphoinositide-dependent-1 kinase inhibitors as antifungal molecules," ACS Chem. Biol. 6(5):502-10 (2011).
Bicanic et al., "Fungal burden, early fungicidal activity, and outcome in cryptococcal meningitis in antiretroviral-naïve or antiretroviral experienced patients treated with amphotericin B or fluconazole," Clin. Infect. Dis. 45:76-80 (2007).
Biondi, et al., "High resolution crystal structure of the human PDK1 catalytic domain defines the regulatory phosphopeptide docking site," EMBO J 21:4219-28 (2002).
Carroll et al., "Mammalian model hosts of cryptococcal infection," Comp. Med. 57:9-17 (2007).
Casamayor et al., "Functional counterparts of mammalian protein kinase PDK1 and SGK in budding yeast," Curr. Biol. 9:186-97 (1999).
Chen et al., "Function and regulation of MAPK signaling pathways: lessons learned from the yeast *Saccharomyces cerevisiae*," Biochim. Biophys. Acta 1773:1311-40 (2007).
Clancy et al., "Animal models of candidiasis," Methods Mol. Biol. 499:65-76 (2009).
Denning et al., "Therapy for fungal diseases: opportunities and priorities," Trends Microbiol. 18:195-204 (2010).
Didone et al., "A high-throughput assay of yeast lysis for drug discovery and genetic analysis," Nat. Protocol. 5:1107-14 (2010).
Dolan et al., "The antifungal activity of tamoxifen: in vitro, in vivo, and mechanistic characterization," Antimicrob. Agents Chemother. 53: 3337-46 (2009).
Dulic et al., "Yeast endocytosis assays," Methods Enzymol. 194:697-710 (1991).
Eglen et al., "The current status of drug discovery against the human kinome," Assay Drug Dev. Technol. 7:22-43 (2009).
Feldman et al., "Novel small molecule inhibitors of 3-phosphoinositide-dependent kinase-1," J. Biol. Chem. 280:19867-74 (2005).
Friant et al., "Sphingoid base signaling via Pkh kinases is required for endocytosis in yeast," EMBO J. 20:6783-92 (2001).
Gelperin et al., "Biochemical and genetic analysis of the yeast proteome with a movable ORF collection," Genes Dev. 19:2816-26 (2005).
Gerik et al., "Pkc1 is essential for protection against both oxidative and nitrosative stresses, cell integrity, and normal manifestations of virulence factors in the pathogenic fungus *Cryptococcus neoformans*," Eukaryot. Cell 7:1685-98 (2008).
Giaver et al., "Genomic profiling of drug sensitivities via induced haploinsufficiency," Nat. Genet. 21:278-83 (1995).
Granville et al., "Handicapping the race to develop inhibitors of the phosphoinositide-3-kinase/Akt/mammalian target of rapamycin pathway," Clin. Cancer Res. 12:679-89 (2006).
Graybill et al., "Addition of caspofungin to fluconazole does not improve outcome in murine candidiasis," Antimicrob. Agents Chemother. 47:2373-5 (2003).
Gutierrez-Escribo et al., "CDK-dependent phosphorylation of Mob2 is essential for hyphal development in *Candida albicans*," Mol. Biol. Cell 22:2458-69 (2011).
Heinisch, "Baker's yeast as a tool for the development of antifungal kinase inhibitors-targeting protein kinase C and the cell integrity pathway," Biochim. Biophys. Acta 1754:171-82 (2005).
Hotte et al., "Phase I clinical trial of UCN-01 in combination with topotecan in patients with advanced solid cancers: a Princess Margaret Hospital phase II consortium study," Ann. Oncol. 17:334-40 (2006).
Inagaki et al., "PDK1 homologs activate Pkc1-mitogen-activated protein kinase pathway in yeast," Mol. Cell. Biol. 19:8344-52 (1999).
Islam et al. "Indolinone based phosphoinositide-dependent kinase-1 (PDK1) inhibitors. Part 1: Design, synthesis, and biological activity," Bioorg. Med. Chem. Lett. 17:3814-8 (2007).
Islam et al., "Indolinone based phosphoinositide-dependent kinase-1 (PDK1) inhibitors. Part 2: Optimization of BX-517," Bioorg. Med. Chem. Lett. 17:3819-25 (2007).
Johnson et al., "A novel celecoxib derivative, OSU03012, induces cytotoxicity in primary CLL cells and transformed B-cell lymphoma cell line via a caspase- and Bcl-2-independent mechanism," Neoplasia 105:2504-2509 (2005).
Jung et al., "Regulation of the yeast Rlm1 transcription factor by the Mpk1 cell wall integrity MAP kinase," Mol. Microbiol. 46:781-9 (2002).
Kim et al., "An isoquinolinium derivative selectively inhibits MAPK Spc1 of the stress-activated MAPK cascade of *Schizosaccharomyces pombe*," Chem. Biol. 13:881-9 (2006).
Knight et al., "Chemical genetics: where genetics and pharmacology meet," Cell 128:425-30 (2007).
Kojic and Darouiche, "*Candida* infections of medical devices," Clin. Microbiol. Rev. 17:255-267 (2004).
Komander et al., "Structural basis for UCN-01 (7-hydroxystaurosporine) specificity and PDK1 (3-phosphoinositide-dependent protein kinase-1) inhibition," Biochem J. 375:255-62 (2003).
Koul et al., "Inhibition of Akt survival pathway by a small-molecule inhibitor in human glioblastoma," Mol. Cancer Ther. 5:637-644 (2006).
Krysan and DiDone, "A high-throughput screening assay for small molecules that disrupt yeast cell integrity," J. Biomol. Screen 13:657-664 (2008).
LaFayette et al., "Pkc signaling regulates drug resistance of the fungal pathogen *Candida albicans* via circuitry comprised of Mkc1, calcineurin and Hsp90," PLoS Path. 6:e1001069 (2010).
Larsen et al., "Amphotericin B and fluconazole, a potent combination therapy for cryptococcal meningitis," Antimicrob. Agents Chemother. 48:985-991 (2004).
Lawlor et al., "Essential role of PDK1 in regulating cell size and development in mice," EMBO J 21:3728-3738 (2002).
Leusch et al., "A genome-wide overexpression screen in yeast for small-molecule target identification," Chem Biol 12:55-63 (2005).
Levin, "Cell wall integrity signaling in *S. cerevisiae*," Microbiol. Mol. Biol. Rev. 69:262-91 (2005).
Liu et al., "Systemic genetic analysis of virulence in the human fungal pathogen *Cryptococcus neoformans*," Cell 135:174-88 (2008).
Liu et al., "The protein kinase CaSch9p is required for the cell growth, filamentation, and virulence in the human fungal pathogen *Candida albicans*," FEMS Yeast Res. 10:462-70 (2010).
Luo et al., "The sphingolipid long chain base-Pkh1/2-Ypk1/2 signaling pathway regulates eisosome assembly and turnover," J. Biol. Chem. 283:10433-44 (2008).
Mukherjee et al., "Combination treatment of invasive fungal infections," Clin. Microbiol. Rev. 18:163-94 (2005).
Nagashima et al., "Genetic and pharmacological inhibition of PDK1 in cancer cells: characterization of a selective allosteric kinase inhibitor," J. Biol. Chem. 286:6433-48 (2011).
Najvar et al., "An alternative animal model for comparison of treatments for cryptococcal meningitis," Antimicrob. Agents Chemother. 43:413-4 (1999).
National Committee for Clinical Laboratory Standards. Reference method for broth dilution antifungal susceptibility testing of yeasts. Approved standard M27-A3, National Committee for Clinical Laboratory Standards, Wayne, PA (2002).
Pandeya et al., "Biological activities of isatin and its derivatives," Acta Pharma 55:27-46 (2005).

\* cited by examiner

KP-372

*Candida* MIC: 3-25 µg/mL

OSU-03012

*C. albicans* MIC 3 µg/mL
*C. neoformans* MIC 4 µg/mL

TREATMENT OR PREVENTION OF FUNGAL INFECTIONS WITH PDK1 INHIBITORS

CROSS-REFERENCE TO RELATED APPLICATION

This application claims the benefit of U.S. Provisional Application No. 61/414,660, filed on Nov. 17, 2010, which is incorporated by reference herein in its entirety.

STATEMENT REGARDING FEDERALLY FUNDED RESEARCH

This invention was made with government funding under Grant No. RO1 AI075033 from the National Institutes of Health. The government has certain rights in this invention.

BACKGROUND

Fungal infections are an increasingly common cause of morbidity and mortality for patients with compromised immune function. Current antifungal drug therapy is quite limited, particularly when compared to antibacterial therapy. Essentially, there are only three mechanistic classes used to treat life-threatening fungal infection and two of these classes have significant toxicities and drug-drug interactions that limit their use. In addition, resistance to the current therapies has been reported and will likely increase in prevalence.

SUMMARY

Provided herein are methods of treating or preventing a fungal infection in a subject. The methods comprise identifying a subject with or at risk of developing a fungal infection and administering to the subject a therapeutically effective amount of an inhibitor of a fungal phosphoinositide dependent kinase 1 (PDK1) or a homolog thereof. Inhibition of the fungal PDK1 or homolog thereof results in the treatment or prevention of the fungal infection in the subject.

Also provided are compositions comprising inhibitors of a fungal phosphosinositide dependent kinase 1 (PDK1) or a homolog thereof and a pharmaceutically acceptable carrier.

The details of one or more embodiments are set forth in the accompanying drawings and the description below. Other features, objects, and advantages will be apparent from the description and drawings, and from the claims.

DESCRIPTION OF DRAWINGS

FIG. 1 shows a screen of a protein kinase library identifies fungilytic molecules.

FIG. 2 shows KP-372-1 blocks CWI pathway signaling.

FIG. 3 shows KP-372-1 has activity against pathogenic yeast and *C. albicans* biofilms.

FIG. 5 shows KP-372-1 inhibits Pil1-GFP phosphorylation, eisosome assembly, and endocytosis in *S. cerevisiae*.

FIG. 6 shows structurally diverse PDK1 inhibitors display antifungal activity.

FIG. 7 shows molecular images of KP-372-1 and OSU-03012.

FIG. 9 shows OSU-03012 is fungicidal in combination with fluconazole and displays in vivo activity.

DETAILED DESCRIPTION

Figure 1A:
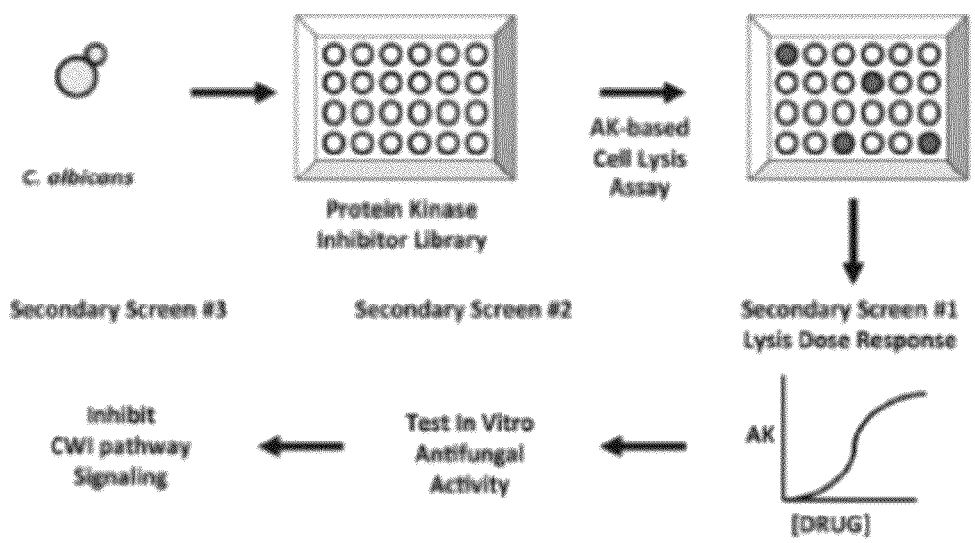
FIG. 1A shows a schematic diagram of the screening strategy. AK=adenylate kinase; CWI=cell wall integrity.

Provided herein are methods of treating or preventing a fungal infection in a subject. The methods comprise identifying a subject with or at risk of developing a fungal infection and administering to the subject a therapeutically effective amount of an inhibitor of a fungal phosphoinositide-dependent kinase 1 (PDK1) or a homolog thereof. Inhibition of the fungal PDK1 or homolog thereof results in the treatment or prevention of the fungal infection in the subject.

Optionally, the PDK1 homolog is phosphoinositide-dependent kinase homolog 1 (Pkh1) or phosphoinositide-dependent kinase homolog 2 (Pkh2) By way of example, in *Saccharomyces cerevisiae* there are two PDK1 homologs, PKH1 and PKH2. By way of another example, in *Candida albicans* there are two PDK1 homologs, PKH1/2. By way of another example, in *Cryptococcus neoformans* there are two PDK1 homologs, PKH2-01 and PKH2-02.

Optionally, the fungal infection is caused by a fungus selected from the group consisting of a *Candida* spp., a *Cryptococcus* spp., an *Aspergillus* spp., a *Nocardia* spp., and a *Saccharomyces* spp. The fungal infection can be caused by a member of the *Candida* spp. selected from the group consisting of *Candida albicans, Candida glabrata, Candida parapsilosis, Candida dubliensis, Candida tropicalis, Candida lusitaniae, Candida pseudoguillerimondi*, and *Candida krusei*. Optionally the fungal infection can be caused by a member of the *Cryptococcus* spp., for example, *Cryptococcus neoformans*.

Optionally, the subject is administered a therapeutically effective amount of KP-372-1. Optionally, the subject is administered a therapeutically effective amount of OSU-03012 or a derivative thereof. The subject can, for example, be administered any dose of at least 3 mg/kg to 200 mg/kg (e.g., 100 mg/kg), inclusively, and any amount in between, of either KP-372-1 or OSU-03012. Derivatives of OSU-03012 are known in the art, e.g., see Zhu et al., Canc. Res. 64:4309-18 (2004).

Optionally, the subject is further administered a therapeutically effective amount of fluconazole. The subject can, for example, be administered any dose of at least 3 mg/kg to 200 mg/kg (e.g., 100 mg/kg), inclusively, and any amount in between, of fluconazole. The subject can, for example, be administered a dose of fluconazole, wherein the dose ranges from about 2 µg/ml to about 20 µg/ml. Optionally, the subject is administered a 4 µg/ml dose of fluconazole. Optionally, the subject is administered a 2 µg/ml dose of fluconazole. Optionally, the subject is administered at least 100 milligrams of fluconazole. Optionally, the subject is administered about 100 to about 1000 milligrams of fluconazole in one administration or in multiple administrations. Administrations can be repeated as necessary or desired.

The inhibitor of fungal PDK1 or a homolog thereof can, for example, inhibit the expression of fungal PDK1 or a homolog thereof. Optionally, the inhibitor of fungal PDK1 or homolog thereof can, for example, block the activity of PDK1 or homolog thereof. For example, the inhibitor can block the phosphorylation of a target of PDK1 or a target of the PDK1 homolog.

Provided herein are compositions comprising an inhibitor of fungal PDK1 or a homolog thereof and a pharmaceutically acceptable carrier. Optionally, the compositions comprise KP-372-1 or OSU-03012 or derivatives thereof and a pharmaceutically acceptable carrier described herein. Optionally, the compositions further comprise fluconazole. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in Remington: *The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Sustained release preparations can be configured into medical devices (e.g., orthopedic devices like pins, screws, joints) that elute the agent. Matrices are in the form of shaped articles, e.g., films, liposomes, or microparticles. Certain carriers may be more preferable depending upon, for instance, the route of administration and concentration of composition being administered. Carriers are those suitable for administration of the agent, e.g., the small molecule, polypeptide, nucleic acid molecule, and/or peptidomimetic, to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. The compositions can also be administered locally including, for example, during surgery. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

As used throughout, the subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a fungal infection (e.g., infection with *Candida* spp., *Cryptococcus* spp., *Aspergillus* spp., *Nocardia* spp., or *Saccharomyces* spp.). The term patient or subject includes human and veterinary subjects.

A subject at risk of developing a fungal infection can, for example, have risk factors for fungal infections (e.g., have damaged or moist skin, have chronic disease, and/or be immunocompromised). A subject at risk for developing a fungal infection can, for example, be exposed to a fungus due to employment (e.g., a healthcare worker), extracurricular activities (e.g., sports), or due to the prevalence of a fungus at a specific location (e.g., a hospital, gymnasium, day care center, prison, or nursing home). A subject currently with a fungal infection has one or more than one symptoms of the infection and may have been diagnosed with the fungal infection.

The methods and agents as described herein are useful for both prophylactic and therapeutic treatment. For prophylactic use, a therapeutically effective amount of the agents described herein are administered to a subject prior to onset (e.g., before obvious signs of a fungal infection) or during early onset (e.g., upon initial signs and symptoms of a fungal infection). Prophylactic administration can occur for several days to years prior to the manifestation of symptoms of a fungal infection. Prophylactic administration can be used, for example, in the preventative treatment of subjects at risk for developing a fungal infection. Therapeutic treatment involves administering to a subject a therapeutically effective amount of the compounds described herein after diagnosis or development of a fungal infection.

According to the methods taught herein, the subject is administered an effective amount of the agent. The terms effective amount and effective dosage are used interchangeably. The term effective amount is defined as any amount necessary to produce a desired physiologic response (e.g., prevention, reduction or elimination of fungal infection). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refer to a method of reducing the effects of a fungal infection or condition or symptom of the fungal infection. Thus in the disclosed method, treatment can refer to a 10%, 20%, 30%, 40%, 50%, 60%, 70%, 80%, 90%, or 100% reduction in the severity of an established fungal infection or symptom of the fungal infection. For example, a method for treating a fungal infection is considered to be a treatment if there is a 10% reduction in one or more symptoms of the fungal infection in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection, condition, or symptoms of the infection or condition.

As used herein, the terms prevent, preventing, and prevention of a fungal infection refer to an action, for example, administration of a compound described herein, that occurs before or at about the same time a subject begins to show one or more symptoms of the fungal infection, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Methods

Yeast Strains, Plasmids, Culture Media and Reagents.
The reporter plasmid pRLM1-lacZ was previously described (Jung et al., Mol. Microbiol. 46:781-9 (2002)).

pGAL-PKH2 was previously described (Gelperin et al., Genes Dev. 19:2816-26 (2005)). The InhibitorSelect library of protein kinase inhibitors was obtained from EMD Chemicals USA (Philadelphia, Pa.). Compounds for re-testing were obtained from separate lots or from alternative suppliers. All compounds and reagents were used as received.

Adenylate Kinase (AK) Assay.

AK assays were performed according to a recently published protocol (Didone et al., Nat. Protocol. 5:1107-14 (2010)) using the 96-well plate version using the Toxi-Light Assay kit (Lonza; Basel, Switzerland). Luminescence was measured using a SpectraMax plate reader (Molecular Devices; Sunnyvale, Calif.). Screening hits were defined as molecules inducing >3-fold increase in RLU relative to wells containing cells treated with 1% dimethylsulfoxide (DMSO).

Antifungal Susceptibility Assays.

The antifungal activity of protein kinase inhibitors was determined using the Clinical and Laboratory Science Institute microdilution protocol M-27A2. Biofilm antifungal activity was determined using the protocol of Pierce et al. and is reported as $MIC_{50}S$ (Pierce et al., Nat. Protoc. 3:1494-1500 (2008)). Disk diffusion assays were performed as described previously (Roelants et al., Microbiology 150:3289-304 (2004)).

β-Galactosidase Reporter Assays.

Logarithmic phase *S. cerevisiae* (BY4741) cells harboring the pRLM1-lacZ plasmid were transferred to a 96-well plate, and treated with Calcofluor white (25 mg/mL)+/−protein kinase inhibitor at sub-inhibitory concentrations (1/2MIC). The cells were incubated at room temperature for 5 hours and processed for β-galactosidase activity using the ThermoScientific Yeast β-galactosidase kit according to the manufacturer's instructions (Pierce; Rockford, Ill.). β-galactosidase activity was determined by measuring $OD_{420}$ using a SpectraMax Plate reader (Molecular Devices) and expressed as fold change in Miller units (nmole/mg/min) relative to untreated cells. Each experiment was performed in duplicate with three independent isolates.

Pil1 Immunobloting.

Western blot analysis of Pil1-GFP was performed essentially as described (Luo et al., J. Biol. Chem. 283:10433-44 (2008)). Briefly, Pil1-GFP containing cells were harvested and lysed using the SDS-PAGE sample buffer method. Extracts corresponding to equivalent numbers of cells were fractionated by SDS-PAGE electrophoresis on 7% gels, transferred to nitrocellulose and blocked overnight in 50 mM Tris pH 7.5/150 mM NaCl/0.05% (v/v) Tween-20+5% (w/v) nonfat skim milk. Pil1-GFP was detected using mouse anti-GFP (1:10,000 dilution, Clontech Living Colors) (Clontech; Mountain View, Calif.) as primary and goat anti-mouse antibodies conjugated with horse-radish peroxidase (1:10,000) followed by visualization with ECL-Plus reagents (Amersham; Piscataway, N.J.).

Microscopy.

Light and fluorescence microscopy was performed using a Nikon ES80 epi-fluorescence microscope equipped with a CoolSnap CCD camera. Images were collected using NIS-Elements Software and processed in PhotoShop. All images were collected with identical exposure settings and equally processed with respect to tone and contrast.

Lucifer Yellow (LY) Endocytosis Assays.

LY uptake assays were performed as described previously (Dulic et al., Methods Enzymol. 194:697-710 (1991)) using LY obtained from Sigma (St. Louis, Mo.). Briefly, yeast cells were grown to logarithmic phase, treated with either 10 mM KP-372-1 or 1% DMSO and incubated for 1 hour. Cells were then exposed to LY and aliquots were removed at 15 minute intervals. Endocytosis was stopped by the addition of sodium azide/succinate and the percentage of cells with vacuolar LY staining was determined by fluorescence microscopy.

Results

PDK1 Inhibitor KP-372 Blocks Cell Wall Integrity Signaling in Yeast.

To identify PKIs that disrupt yeast cell wall integrity, a four-part screening strategy as outlined in FIG. 1A was designed. The primary screen in the approach detects molecules that cause yeast cells to lyse, a characteristic phenotype of yeast cell wall damage, by use of an assay that detects the release of adenylate kinase (AK) to the growth medium as a reporter of yeast cell lysis. Previously it was shown that the AK assay in HTS format can detect as few as 500 lysed yeast cells in a sample of $10^5$ cells (Didone et al., Nat. Protocol. 5:1107-14 (2010)). PKIs that cause yeast cells lysis (hits) were then re-confirmed by AK dose-response assays and tested for in vitro antifungal activity against the human fungal pathogen *C. albicans* using standard microdilution susceptibility testing. Last, to select PKIs specific for the CWI signaling pathway, the set of hits were tested for their ability to block the activation of a transcriptional reporter of the CWI-signaling pathway.

Figure 1B:
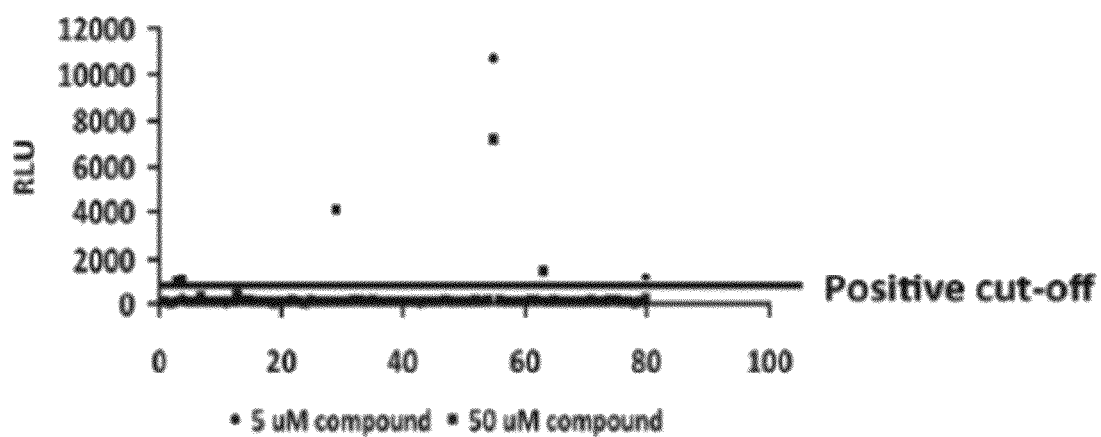
FIG. 1B shows a scatter plot of primary AK assay screening data. Data points above the line represent >3 fold increase in relative light units (RLU) of AK activity and were scored as positive.

To rapidly survey a sample of well-characterized PKIs, the commercially available InhibitorSelect collection, a library of 80 PKIs with diverse mechanistic and structural characteristics, was utilized. *C. albicans* clinical reference strain SC5314 was screened against the InhibitorSelect library for molecules that caused a release of AK into the growth medium. Compounds were screened at 5 mM and 50 mM concentrations and a compound was scored as positive if it induced a three-fold increase in extracellular AK activity relative to DMSO-treated cells. A scatter plot of the raw screening data is shown in FIG. 1B. As summarized in Table 1, eight protein kinase inhibitors caused *C. albicans* cell lysis (hit rate 10%) and possessed good in vitro activity against *C. albicans* by growth assays (Minimum Inhibitory Concentration (MIC), 3-20 µg/mL). Four hits were PKIs previously shown to have antifungal activity (staurosporine, chelerythine, rapamycin, and heribmycin) and these served to confirm the validity of the screening approach. The set of four novel hits included three molecules (Akt IV, Akt V, & KP-372-1) that target the AGC family-derived PIK3/PDK1/Akt signaling network in mammalian cells (Granville et al., Clin. Cancer Res. 12:679-89 (2006)) and one molecule that targets tyrosine kinases (Syk II) (Weinblatt et al., N. Engl. J. Med. 363:1303-12 (2010)). Although the library contained a number of MAPK inhibitors, none were identified in the screen. This is likely due to the fact that MAPKs are not essential genes in either *S. cerevisiae* or *C. albicans* (Levin, Microbiol. Mol. Biol. Rev. 69:262-91 (2005)).

TABLE 1

Set of hits enriched for AGC family kinase inhibitors.

| Inhibitor | Fold increase in AK release | MIC (µg/ml) | Mechanism | AGC family | Known Antifungal |
|---|---|---|---|---|---|
| Akt IV | 12 | 9 | Akt/Pkb | Yes | No |
| Akt V | 12 | ND | Akt/Pkb | Yes | No |
| PDK1/Akt (KP-372-1) | 4 | 3 | PDK1/Akt | Yes | No |
| Chelerythine | 5 | 125 | Pkc1 | Yes | Yes |
| Staurosporine | 48 | 0.5 | Pkc1 | Yes | Yes |
| Herbymicin | 127 | 40 | Hsp90 | No | Yes |

TABLE 1-continued

Set of hits enriched for AGC family kinase inhibitors.

| Inhibitor | Fold increase in AK release | MIC (µg/ml) | Mechanism | AGC family | Known Antifungal |
|---|---|---|---|---|---|
| Rapamycin | 17 | 100 | TOR | No | Yes |
| SykII | 14 | 9 | Tyrosine kinase | No | No |

Figure 2A:
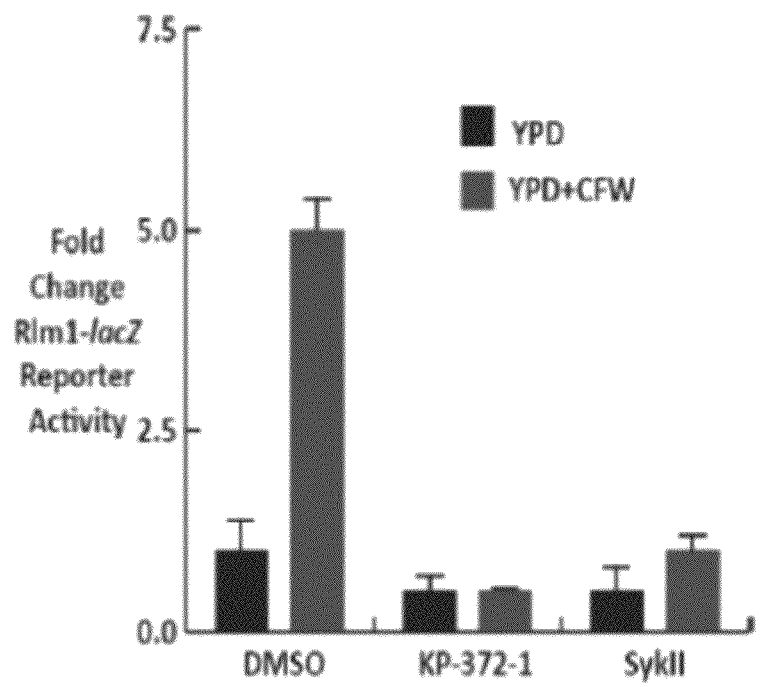
FIG. 2A shows a graph demonstrating CWI pathway reporter Rlm1-lacZ activity in *S. cerevisiae* induced by calcofluor white±sublethal concentrations (1/2 MIC) KP-372-1 and SykII. Bars indicate mean fold change in Miller units of β-galactosidase activity relative to logarithmic phase cells without calcofluor or PKI. Error bars indicate standard deviation of three independent trials performed in triplicate.

The novel, antifungal PKIs identified in the primary screen were evaluated for their ability to block CWI pathway signaling using a reporter construct that contains two copies of the consensus binding site for the CWI-pathway-regulated transcription factor Rlm1 fused to the β-galactosidase gene (Jung et al., Mol. Microbiol. 46:781-9 (2002)). A plasmid containing RLM1-lacZ was transformed into the model yeast *S. cerevisiae*. The chitin binding agent Calcofluor white (CFW), a well-characterized inducer of cell wall stress, was used to activate reporter activity. Sub-inhibitory concentrations of both KP-372-1 and SykII completely abolished reporter activity induced by CFW (FIG. 2A). The Akt inhibitors had no effect on reporter activity, a finding consistent with the fact that the yeast Akt homolog, Sch9, has not been previously linked to CWI-pathway signaling (Zeng et al., Cancer Res. 66:3737-46 (2006)). These data validate the utility of the screening strategy and provide two new structural classes of potential cell wall-targeted antifungal small molecules.

KP-372-1 is a dual PDK1/Akt inhibitor with anti-cancer properties (Pierce et al., Nat. Protoc. 3:1494-1500 (2008)) while SykII is a tyrosine kinase inhibitor that has been developed as an approach to the treatment of auto-immune diseases (Weinblatt et al., N. Engl. J. Med. 363:1303-12 (2010)). KP-372-1 has been shown to have potent activity against both leukemic and glioblastoma cells but is tolerated by normal cells at micromolar concentrations without significant cytotoxicity (Pierce et al., Nat. Protoc. 3:1494-1500 (2008)). Consistent with its low cytotoxicity toward normal cells, KP-372-1 has been screened against a large panel of human protein kinases and found to have at least 10-fold selectivity for a limited number of human kinases. Therefore, the antifungal activity of KP-372-1 was investigated further.

Figure 2B:
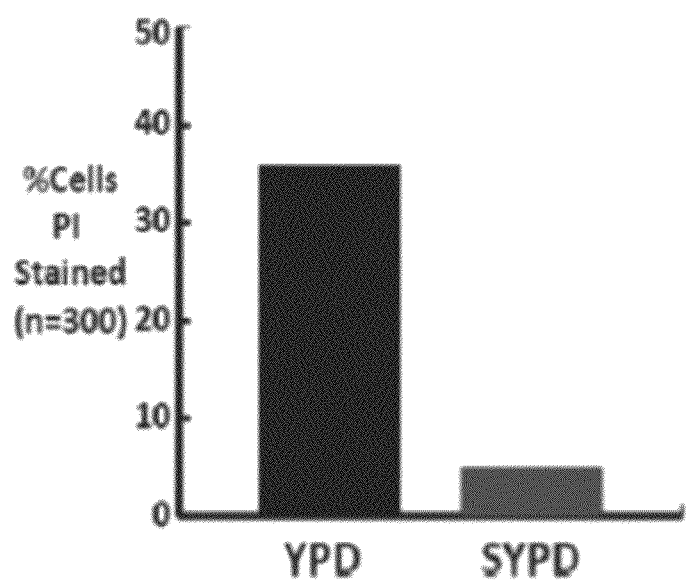
FIG. 2B shows a graph of the results of *C. albicans* cells treated with KP-372-1 at MIC for 2 hours at 37° C. in YPD or YPD+1 M sorbitol (SYPD) and stained with propidium iodide. The percentage of cells with PI uptake was determined by fluorescence.

A hallmark phenotype of mutations and drugs that interfere with CWI signaling is that their effects can be suppressed by the addition of osmotic support such as 1M soribitol to the culture medium. By equalizing the osmotic gradient across the plasma membrane, cell integrity is less dependent upon an intact cell wall. To further confirm that the fungilytic activity of KP-372-1 was due to disruption of cell wall integrity, the effect of 1M sorbitol on the ability of KP-372-1 to kill *C. albicans* was investigated using propidium iodide uptake as a marker of disrupted cellular integrity. As shown in FIG. 2B, 36% of *C. albicans* cells were stained by propidium iodide after 2 hours of KP-372-1 treatment in standard yeast peptone dextrose (YPD) while five-fold fewer cells were stained by propidium iodide in 1M sorbitol-supplemented YPD. This result strongly supports the idea that KP-372-1 targets processes required for yeast cell wall integrity as part of its mode of action.

KP-372-1 is Active Against Non-Albicans *Candida* Spp. and *C. albicans* Biofilms.

Figure 3A:
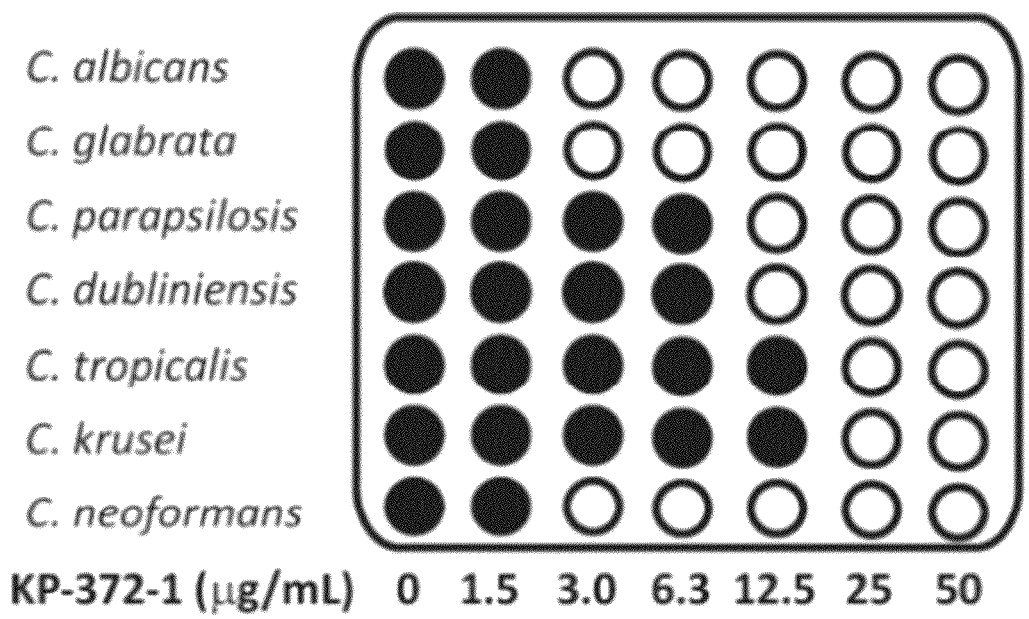
FIG. 3A shows a schematic representation of the MIC of KP-372-1 against pathogenic yeast. Filled circles indicate growth and clear circles indicate no detectable turbidity. The lowest concentration of drug resulting in no growth is defined as the MIC.

To further characterize the in vitro antifungal activity of KP-372-1, the MIC for KP-372-1 was determined for a set of pathogenic *Candida* spp. and *C. neoformans*. KP-372-1 is highly active against the two most common Candida spp., *C. albicans* and *C. glabrata*, while less so toward other *Candida* spp. (FIG. 3A). Importantly, KP-372-1 is highly active against *C. neoformans*. Since the echinocandin class of cell wall-targeted 1,3-β-glucan synthase inhibitors is not active against *C. neoformans*, this represents one of the few cell wall-targeted molecules with activity against this important pathogen.

The combination of KP-372-1 with the clinically-used antifungal drugs fluconazole and caspofungin was examined using checkerboard interaction assays to determine if they showed synergistic activity toward *C. albicans*. This assay allows one to compare the activity of a molecule alone and in combination with another molecule by generating a fractional inhibitory concentration (FIC). FIC for two drugs (A & B) is calculated as follows: $FIC=MIC_A/MIC_{(A+B)}+MIC_B/MIC_{(A+B)}$. FIC values less than 0.5 are considered synergistic; between 0.5 and 1 are additive; between 1-2 are indifferent; and above 2 are antagonistic. The FIC was 0.5 for the combination of KP-372-1 and caspofungin and 1.0 for the combination of KP-372-1 and fluconazole. Therefore, KP-372-1 is not synergistic with either agent.

Figure 3B:
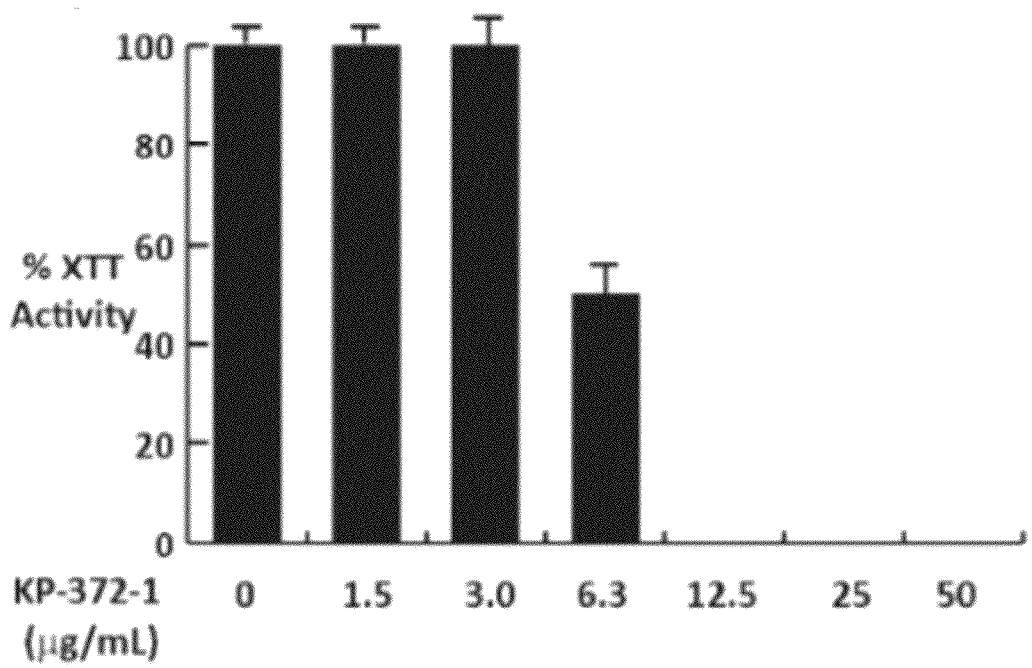
FIG. 3B shows the activity of KP-372-1 against 48-hour *C. albicans* biofilms. Biofilms were generated in 96-well plates by incubation at 37° C. for 48 hours and treated with KP-372-1 for an additional 24 hours. Metabolic activity was determined using the XTT assay. The sMIC$_{50}$ (6.3 µg/mL) is defined as the concentration that reduces metabolic activity by 50% relative to untreated control.

Next, the effect of KP-372-1 on the viability of biofilms that had matured in microtiter plates for 48 hours was determined using the established XTT-reduction based assay of metabolic activity. As shown in FIG. 3B, KP-372-1 has excellent in vitro activity against *C. albicans* biofilms with the $sMIC_{50}$ (3 µg/mL) of KP-372-1 identical to its MIC against planktonic *C. albicans*. Since very few antifungals retain activity against fungal biofilms, these results further suggest that KP-372-1 represents an exciting lead compound with many desirable properties as an antifungal agent.

Yeast Strains with Mutations in PDK1 Orthologs are Hypersensitive to KP-372-1.

As noted above, KP-372-1 has been shown to inhibit both PDK1 and Akt in mammalian cells. Orthologs of PDK1 are present in both the model yeast *S. cerevisiae* and pathogenic fungi and are referred to as PKH genes based on the name assigned to the *S. cerevisiae* family (Casamyayor et al., Curr. Biol. 9:186-97 (1999))). The closest ortholog of Akt in yeast is Sch9 which is also present in *S. cerevisiae* as well pathogenic yeast (Zeng et al., Cancer Res. 66:3737-46 (2006)). Since Sch9 has not been implicated in yeast cell wall integrity nor is it an essential gene, it seemed unlikely that the antifungal activity of KP-372-1 would be due to specific inhibition of the Akt orthologs. In contrast, deletion of both PKH1 and PKH2 is lethal, indicating that the PKH genes carry out essential functions in yeast and suggesting that the PDK1 inhibitory activity of KP-372-1 would be more likely to be responsible for its fungicidal activity than its Akt activity.

Figure 4A:
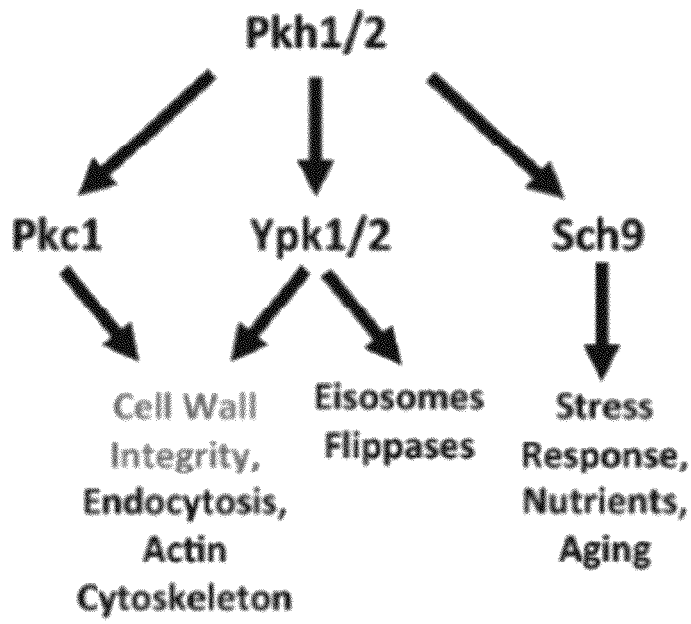
FIG. 4A shows a schematic of kinases and cellular functions regulated by *S. cerevisiae* PDK1 orthologs Pkh1/2. The indicated strains of *S. cerevisiae* (S.c., FIG. 4B) and *C. neoformans* (C.n., FIG. 4C) were inoculated in top agar of YPD plates, and filter discs containing the indicated concentrations of KP-372-1 were placed on the plates. Plates were incubated at 30° C. for 3 days prior to photography.

Therefore, the initial mechanistic studies were focused on testing the hypothesis that KP-372-1 targets PDK1 orthologs in yeast. Although little is known about the function of PKH genes in pathogenic yeast, *S. cerevisiae* Pkh1 and Pkh2 has been studied by a number of groups. ScPKH1&2 are a partially redundant pair of essential kinases that function in cell wall integrity, flippase regulation, endocytosis and eisosome assembly. Like mammalian PDK1, Pkh1/2 phosphorylate and activate downstream kinases including the ACG family kinases Ypk1/2p, Sch9p, and Pkc1p (FIG. 4A). Ypk1/2 and Pkc1p are required for cell wall integrity and activation of the CWI signaling pathway.

Figure 4B:
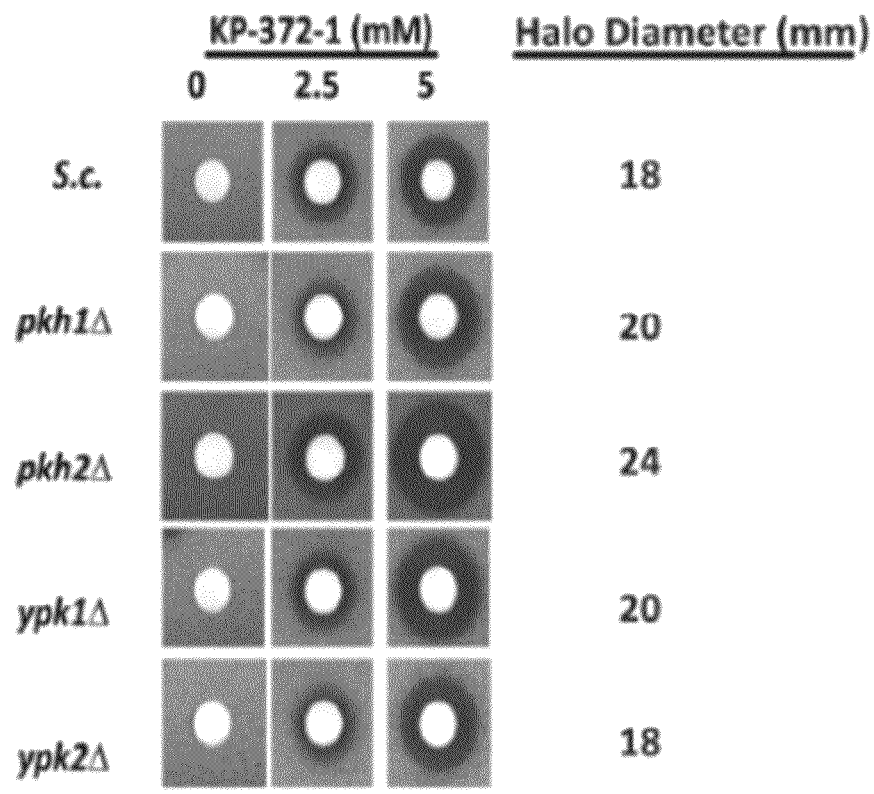
FIG. 4 shows yeast strains with mutations in PDK1 orthologs are hypersensitive to KP-372-1.

Heterozygous diploid yeast mutants lacking one allele of the gene encoding a putative drug target are frequently hypersensitive to the effects of that drug. This is called drug-induced haploinsufficiency. Similarly, if a drug targets the products of two redundant genes, then deletion of one of those genes in a haploid yeast strain will hypersensitize the strain to that drug. Consistent with this phenomena, *S. cerevisiae* pkh2D mutants showed a larger zone of inhibition by disk diffusion assay than wild type or pkh1D (FIG. 4B). Pkh1/2 phosphorylates two other AGC protein kinases involved in yeast cell wall integrity, Ypk1&2. As shown in FIG. 4B, neither ypk1D nor ypk2D is hypersensitive to KP-372-1. The Pkh1/2 kinases function upstream of Ypk1/2 and, thus, if KP-372-1 primarily targets Pkh1/2, then YPK mutants should not be hypersensitive to the drug by epistasis. The fact that the YPK mutants are as sensitive to KP-372-1 as wild type further supports the hypothesis that the drug targets the PDK1 orthologs Pkh1/2.

Figure 4C:
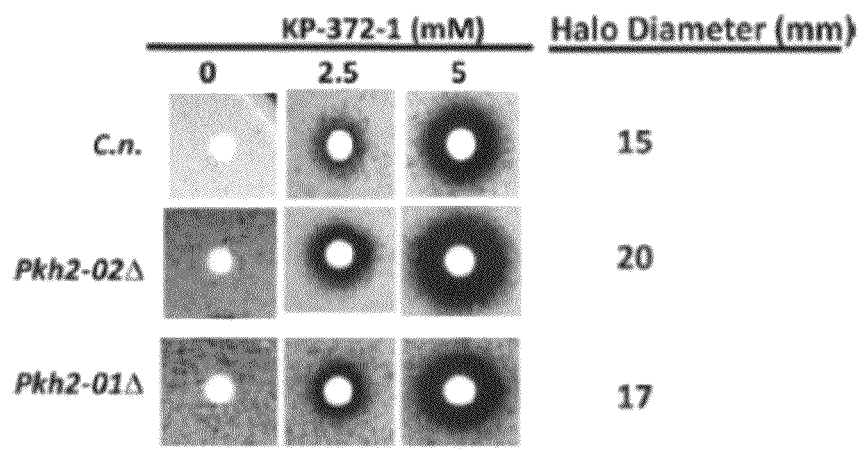

Two PKH analogs, PKH2-01 and PHK2-02, are present in C. neoformans and both deletion mutants are in the large set of deletion mutants recently made publicly available (Liu et al., Cell 135:174-88 (2008)). As part of that project, it was found that PKH2-02 was deficient for growth at 37° C., a virulence property for C. neoformans and, accordingly, showed a strong virulence defect in a mouse model of pulmonary cryptococcosis. The mutants were obtained from this collection and, consistent with the S. cerevisiae mutants, PKH2-02 is significantly more sensitive to KP-372-1 than wild type while PKH2-01 is slightly more sensitive than wild type at 30° C. (FIG. 4C). Although not definitive, these chemical genetic studies strongly support the notion that KP-372-1 targets PDK1 orthologs in yeast as part of its mode of action as an antifungal molecule.

KP-372-1 Inhibits Phosphorylation of the Pkh Substrate Pil1p.

The genetic experiments presented above suggest that the antifungal properties of KP-372-1 are related to its activity as a PDK1 inhibitor. The fact that the PDK1 orthologs Pkh1/2 phosphorylate the eisosome component Pil1 while neither the Akt ortholog Sch9 nor the other downstream kinase targets of Pkh1/2 (Ypk1/2 & Pkc1) are involved in its phosphorylation was used to further test whether the antifungal properties of KP-372-1 are related to its activity as a PDK1 inhibitor. Pil1p is a key component of eisosomes, which are punctate structures located beneath the plasma membrane that may play a role in endocytosis. Pkh1/2-mediated phosphorylation of Pil1 appears to be involved in eisosome regulation. Since Pkh1/2p-mediated phosphorylation of Pil1p generates a species with markedly decreased mobility by SDS-PAGE, this substrate provides an ideal system to test the hypothesis that KP-372-1 inhibits Pkh1/2p in the cell.

S. cerevisiae strains containing a chromosomally-integrated PIL1-GFP allele were transformed with a vector control or a plasmid expressing PKH2 under the control of a galactose-inducible promoter. The resulting strains were grown overnight in raffinose-containing medium to de-repress the galactose promoter and then shifted to galactose-containing medium to induce expression of PKH2 in the presence or absence of sub-inhibitory KP-372-1 (1/2 MIC). The phosphorylation status of Pil1-GFP was followed over a 3.5 hour time course by Western blot.

Figure 5A:
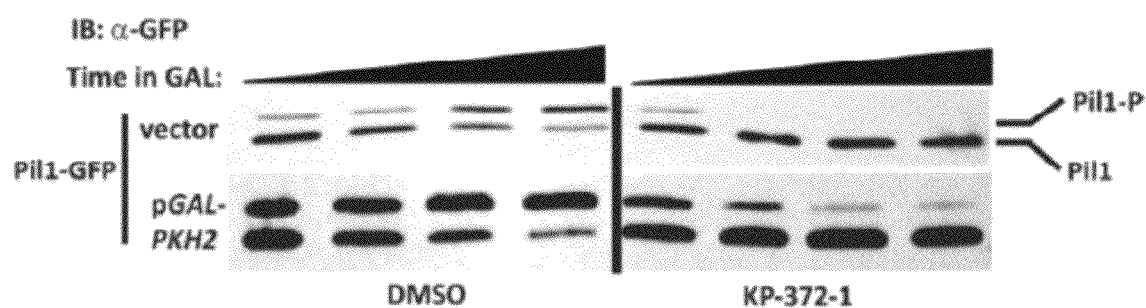
FIG. 5A shows a Western blot from *S. cerevisiae* strains containing a Pil1-GFP allele and either empty plasmid or a plasmid expressing PKH2 from a galactose-inducible promoter that were shifted from raffinose to galactose medium and incubated in the presence or absence of sub-inhibitory KP-372-1 (1/2MIC). Cells were harvested at the indicated times and analyzed by Pil1-GFP immunoblotting. Pil1-P corresponds to the Pkh1/2-dependent phosphorylated Pil1 species.

As shown in FIG. 5A, Pil1-GFP phosphorylation increases as the cells enter into logarithmic phase in untreated strains containing empty vector. Consistent with previously reported observations, galactose-induced, over-expression of PKH2 dramatically increases the proportion of phosphorylated Pil1-GFP compared to vector control (Walther et al., EMBO J 26:4946-55 (2007)). In the presence of KP-372-1, phosphorylation of Pil1-GFP is rapidly blocked in cells with endogenous Pkh1/2 as well as in cells over-expressing Pkh2 Deletion mutants of the Akt ortholog sch9D do not have defects in eisosome assembly and, therefore, the ability of KP-372-1 to block Pil1-GFP phosphorylation cannot be due to its activity as an Akt inhibitor. Accordingly, this experiment indicates that KP-372-1 inhibits PDK1 orthologs in yeast. The data also indicate that a substantial portion of the Pkh1/2 activity is inhibited in KP-372-1-treated cells since none of the Pkh1/2-phosphorylated form of Pil1 was detected; indeed, these blots are similar to those derived from pkh1$^{ts}$ pkh2D cells that have been shifted to the restrictive temperature. Since loss of PDK1 (Pkh1/2) activity in yeast is lethal and loss of Akt activity (Sch9) is not, these data also strongly support the notion that the antifungal activity of KP-372-1 is due in large part to its activity as a PDK1 inhibitor.

KP-372-1 Induces Eisosome Disassembly and Blocks Endocytosis in S. cerevisiae.

Figure 5B:
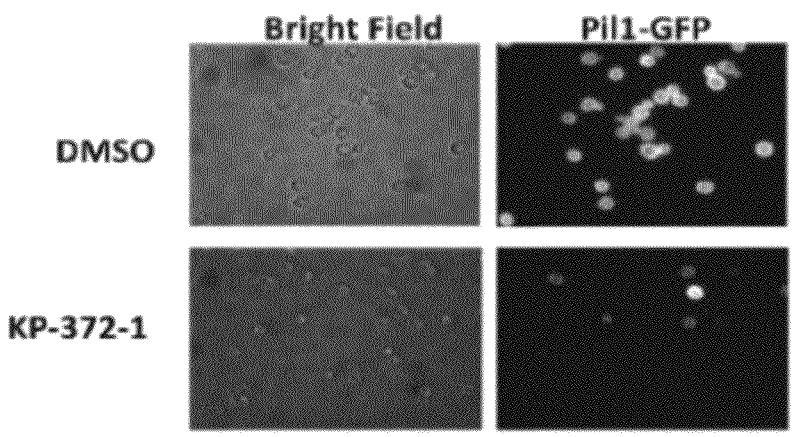
FIG. 5B shows immunofluorescent images of Pil1-GFP strains treated for 3 hours with KP-372-1 (1/2 MIC) or 1% DMSO.

Since significantly reduced Pil1-GFP phosphorylation at sub-lethal concentrations of KP-372-1 was observed, it was hypothesized that the use of this inhibitor as a chemical probe of the role of Pkh1/2 phosphorylation might provide useful information regarding its role in eisosome assembly. Therefore, S. cerevisiae cells containing Pil1 with a C-terminal GFP fusion were treated with KP-372-1 and its effect on eisosome patterns was examined by fluorescence microscopy. As shown in FIG. 5B, DMSO-treated cells show the typical pattern of eisosome distribution. However, within one hour of treatment, the number of peripheral eisosomes dramatically decreased. The micrographs of the KP-372-1-treated cells closely match those previously reported (Luo et al., J. Biol. Chem. 283:10433-44 (2008)) and, consequently, support a model in which Pil1 phosphorylation is required for eisosome assembly/stabilization.

Figure 5C:
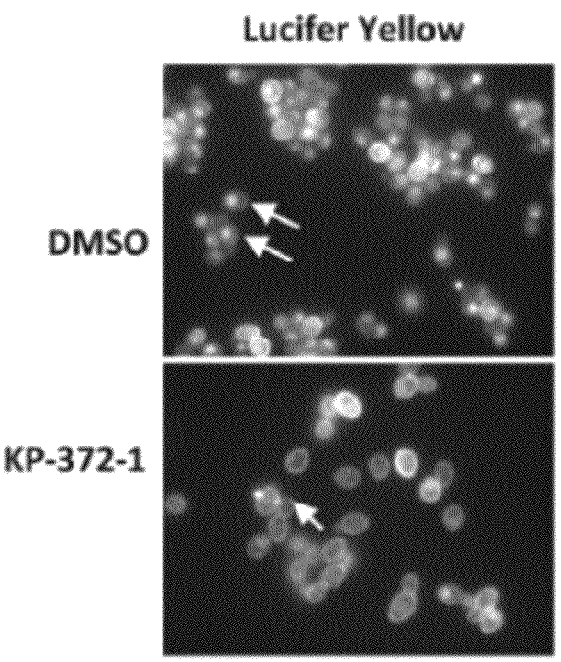
FIG. 5C shows images of *S. cerevisiae* cells treated with either KP-372-1 (1/2 MIC) or 1% DMSO for 1 hour and then processed for Lucifer yellow (LY) uptake. Representative field of cells 15 minutes after addition of LY.
Figure 5D:
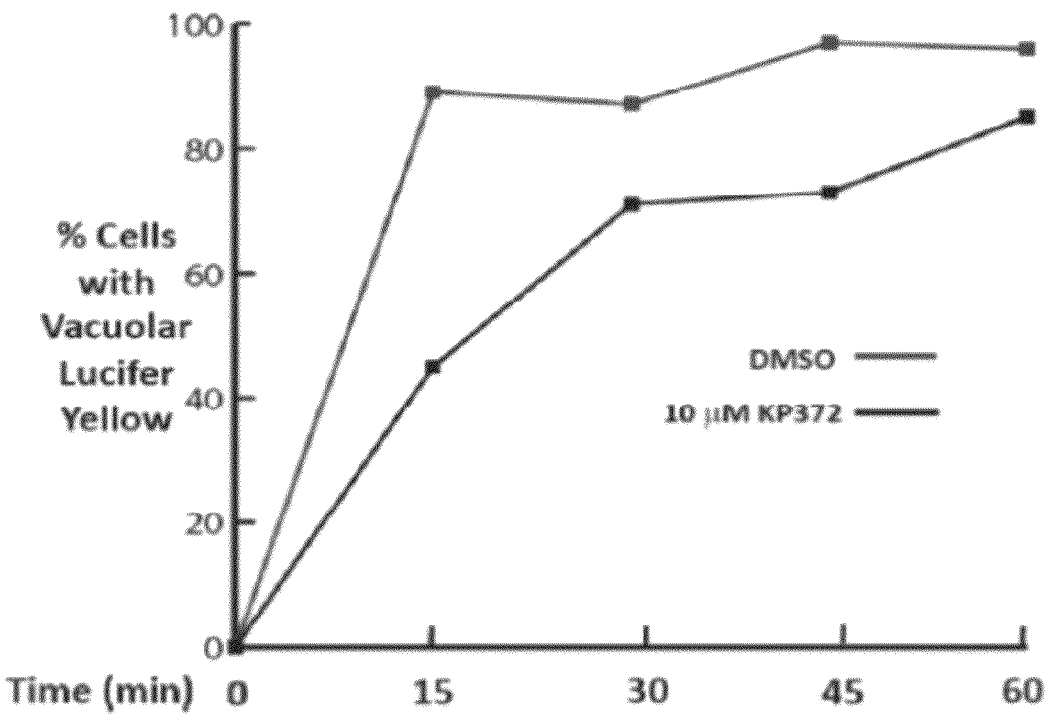
FIG. 5D shows a graph of a time course of LY uptake in the presence or absence of KP-372-1 (standard deviation for each point <10%).

Pkh kinases are also important for endocytosis in yeast. Therefore, the effect of sub-lethal KP-372-1 on fluid-phase endocytosis using a Lucifer yellow (LY) uptake assay was determined. LY binds to the plasma membrane and is transported to the vacuole (yeast lysosomal homolog) in PKH-dependent fashion. As shown in FIG. 5C, fewer KP-372-1-treated cells show vacuolar localization of the dye in comparison to untreated control cells. Scoring vacuolar localization over a 1 hour time course revealed that uptake is inhibited at early time points by KP-372-1 but that the proportion of cells with internalized LY approaches that of untreated cells at later time points (FIG. 5D). Importantly, a substantial number of treated cells eventually internalized LY, indicating that KP-372-1 induced defects in endocytosis and eisosome assembly are unlikely to be due to cell death.

Antifungal Activity of Structurally Distinct PDK1 Inhibitors.

Among the protein kinase inhibitors that have entered clinical development are two molecules with activity toward PDK1, UCN-01 (Hotte et al., Ann. Oncol. 17:334-40 (2006)) and OSU-03012 (Zhu et al., Cancer Res. 64:4309-18 (2004)). In addition, BX-912 has been tested in animal models (Peifer and Alessi, Chem. MedChem. 3:1810-38 (2008)). These compounds are well tolerated and, in general, have low cytotoxicity toward human cells. Since these compounds are commercially available and have favorable pharmacological properties, a focused structure-activity study was carried out to determine whether PDK1 inhibitors based on other chemical scaffolds also display antifungal activity. Scaffolds with antifungal activity could then serve as starting points for further optimization of the antifungal activity of PDK1 inhibitors.

Figure 6A:
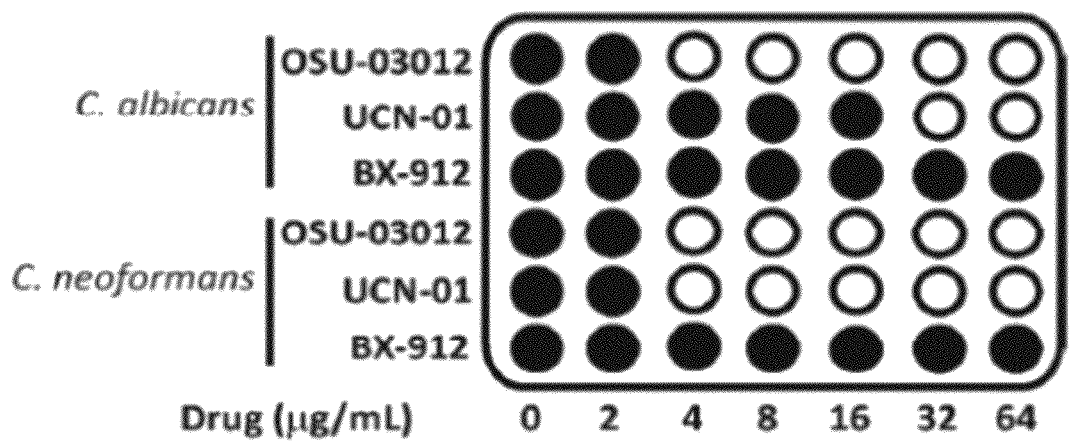
FIG. 6A shows a schematic representation of the minimum inhibitory concentration (MIC) of KP-372-1 against *C. albicans* and *C. neoformans*. Filled circles indicate growth and clear circles indicate no detectable turbidity. The lowest concentration of drug resulting in no growth is defined as the MIC.
Figure 6B:
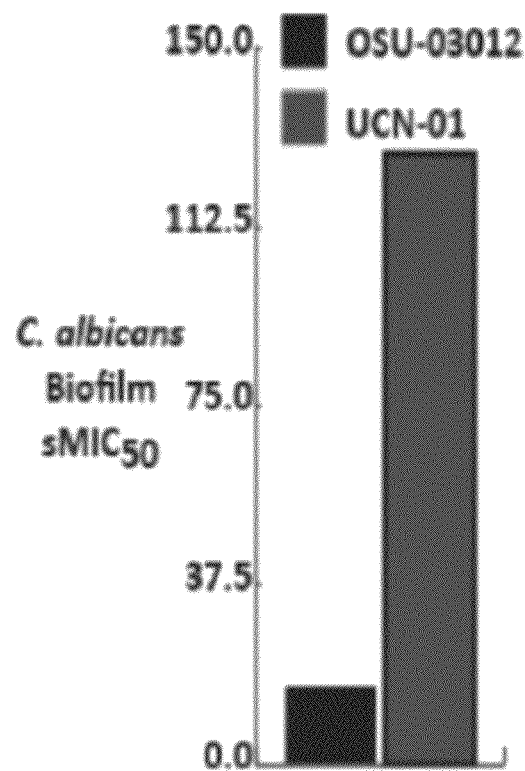
FIG. 6B shows a graph of the sMIC$_{50}$ of OSU-03012 and UCN-01 toward *C. albicans* biofilms as determined by XTT assay.
Figure 7A:
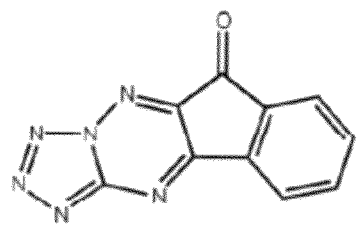
FIG. 7A shows an image of KP-372-1, which has a minimum inhibitory concentration (MIC) of 3-25 µg/ml in *Candida* spp.
Figure 7A:
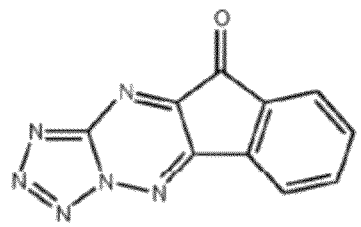
Figure 7B:
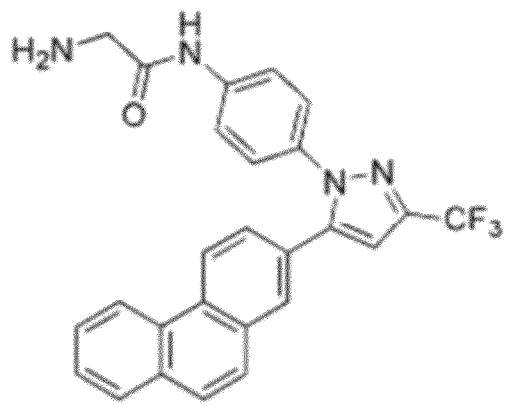
FIG. 7B shows an image of OSU-3012, which has a MIC of 3 µg/ml in *C. albicans* and 4 µg/ml in *C. neoformans*. This molecule is tolerated in human cells at 8 µg/ml.
Figure 8:
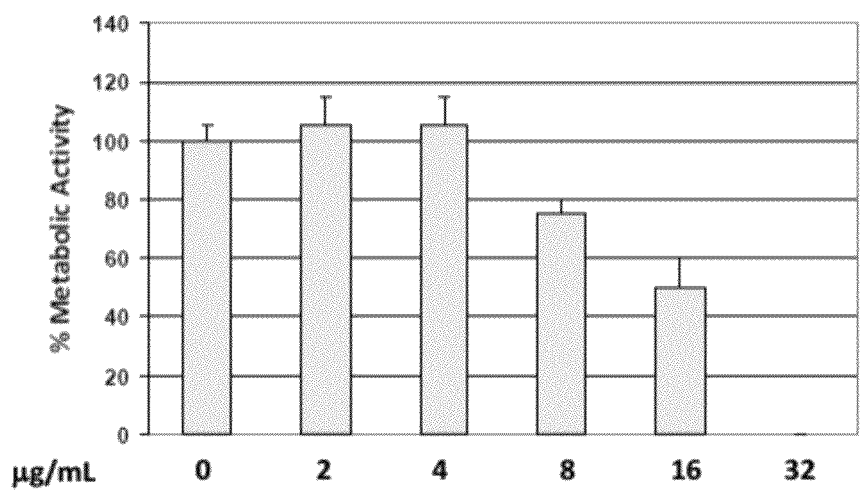
FIG. 8 shows PDK1 inhibitors are active against *C. albicans* biofilms. SC5314 biofilms were generated in microtiter plates for 48 hours and treated with OSU-03012 for 24 hours before being subject to an XTT reduction assay of metabolic activity.

As summarized in FIG. 6A, both UCN-01 and OSU-03012 showed good antifungal activity against C. albicans and C. neoformans while BX-912 did not inhibit growth below 64 μg/mL. In addition, both OSU-03012 and UCN-01 showed activity against C. albicans biofilms (FIG. 6C and FIG. 8), although at higher concentrations than those active against planktonic cells. In contrast to KP-372-1 and OSU-03012, UCN-01 showed synergy with fluconazole (FIC=0.3) but not with caspofungin (FIC=1.0). UCN-01 is a modestly more selective derivative of the promiscuous protein kinase inhibitor staurosporine. Staurosporine has been shown to be synergistic with fluconazole and the synergy displayed by UCN-01 may be due to its structural similarity to staurosporine.

In Vivo Testing of OSU-03012 in Mouse Model of Candidiasis.

Figure 9A:
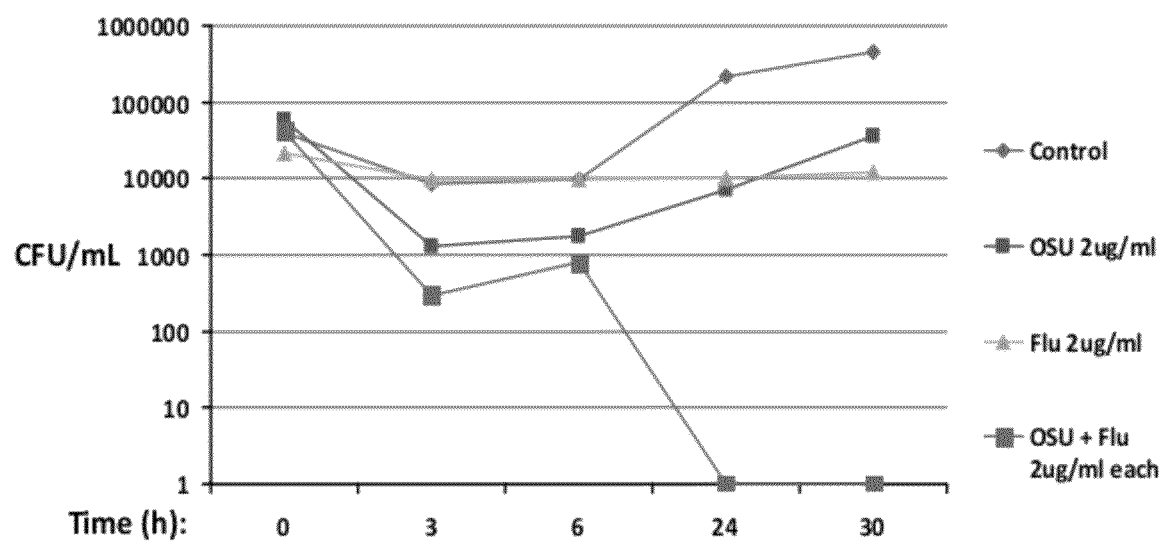
FIG. 9A shows a graph demonstrating that OSU-03012 is synergistic and fungicidal against *C. neoformans* H99 in combination with fluconazole. YPD cultures were incubated at 37° C. for 30 hours in the presence of the indicated drugs and combinations. Aliquots were diluted and plated on YPD at 30° C. to determine inoculum.
Figure 9B:
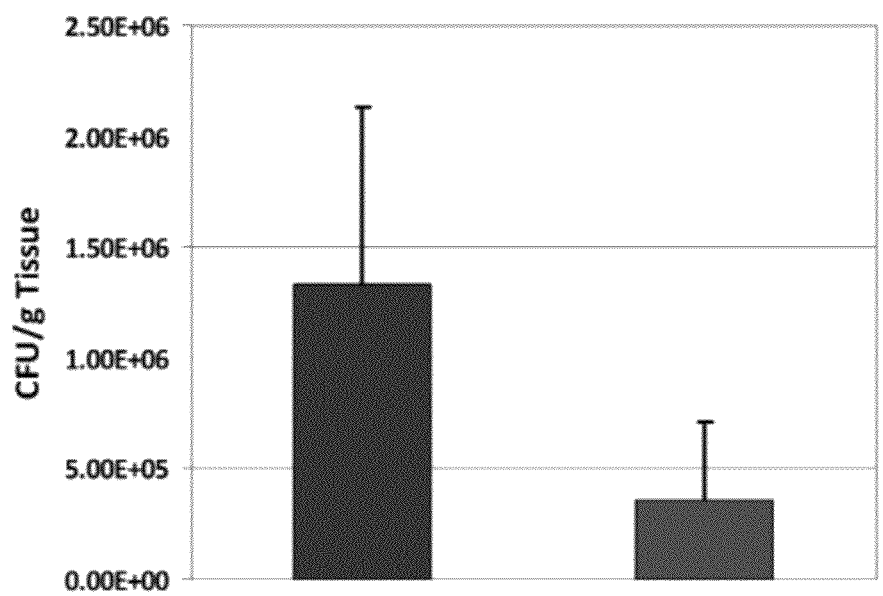
FIG. 9B shows a graph demonstrating in vivo activity of OSU-03012. BALB/c mice (n=5 per group) were treated with 100 mg/kg OSU-03012 per day by oral gavage after inoculation with *C. albicans* SC5314 by tail vein injection for 2 days and kidney fungal burden was determined.

To determine whether OSU-03012 has in vivo activity against *C. albicans* infection, a mouse model of candidiasis was used. On the day of inoculation (DO), BALB/c mice were restrained in a mechanical restrainer and inoculated with *C. albicans* strain SC5314 suspended in saline ($1 \times 10^5$ cfu/animal) via lateral tail vein injection. OSU-03012 (100 mg/kg) in peanut oil was given by gavage to half the animals (n=5) and peanut oil alone was given to the other half of animals on the day of inoculation and on the following day. ON D2, the animals were sacrificed and the kidneys harvested. The kidneys were homogenized and dilutions were plated on yeast peptone dextrose plates containing gentamicin and vancomycin. The plates were incubated at 30° C. for one day and colony forming units per kidney were determined by standard methods. Differences between treatment and no treatment groups were analyzed by Student's t test with a statistically significant effect defined as $P<0.05$. It was determined that OSU-03012 demonstrating in vivo activity against *C. albicans* infection (FIG. 9B).

Time-Kill Evaluation of OSU-03012 in Combination with Fluconazole.

To determine if the combination of OSU-03012 and fluconazole was fungicidal, overnight cultures of *C. neoformas* strain H99 were diluted to $1.5 \times 10^4$ cells/ml in yeast peptone dextrose containing either: dimethyl sulfoxide (DMSO) (1% final concentration); fluconazole (2 µg/ml/1% DMSO); OSU-03012 (2 µg/ml/1% DMSO); or OSU-03012 and fluconazole (2 µg/ml each/1% DMSO). The cultures were incubated at 37° C. for 30 hours. Aliquots were removed at 0, 3, 6, 24, and 30 hours; diluted and plated on yeast peptone dextrose plates. The plates were incubated at 30° C. for 48 hours and colony forming units per ml determined by standard methods. It was determined that the combination of OSU-03012 and fluconazole was fungicidal (FIG. 9A).

What is claimed is:

1. A method of treating a fungal infection in a subject, the method comprising:
   (a) identifying a subject with a fungal infection, and
   (b) administering to the subject a therapeutically effective amount of OSU-03012 and a therapeutically effective amount of fluconazole, wherein the fungal infection is caused by *Cryptococcus neoformans*.

2. The method of claim 1, wherein the subject is administered a dose of 3 mg/kg to 200 mg/kg of OSU-03012.

3. The method of claim 2, wherein the subject is administered a dose of 100 mg/kg of OSU-03012.

* * * * *